(12) United States Patent
Lefebvre et al.

(10) Patent No.: US 9,594,198 B2
(45) Date of Patent: Mar. 14, 2017

(54) OPTICAL FOCUSING DEVICE

(71) Applicant: Commissariat à l'Energie Atomique et aux Energies Alternatives, Paris (FR)

(72) Inventors: Anthony Lefebvre, Seyssinet-Pariset (FR); Salim Boutami, Grenoble (FR)

(73) Assignee: Commissariat à l'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 14/988,853

(22) Filed: Jan. 6, 2016

(65) Prior Publication Data
US 2016/0195649 A1    Jul. 7, 2016

(30) Foreign Application Priority Data

Jan. 6, 2015 (FR) ...................................... 15 50058

(51) Int. Cl.
*G02B 5/18* (2006.01)
*G01N 21/31* (2006.01)
*G01N 21/3504* (2014.01)

(52) U.S. Cl.
CPC ......... *G02B 5/1861* (2013.01); *G01N 21/314* (2013.01); *G01N 21/3504* (2013.01); *G02B 5/1876* (2013.01); *G01N 21/31* (2013.01); *G02B 5/18* (2013.01)

(58) Field of Classification Search
USPC ............................................... 356/432–444
See application file for complete search history.

(56) References Cited

U.S. PATENT DOCUMENTS

| | | | | |
|---|---|---|---|---|
| 4,079,411 A | * | 3/1978 | Engelbrecht | G02B 5/1871 348/291 |
| 4,636,076 A | * | 1/1987 | Pettigrew | G01D 5/38 356/499 |
| 5,361,148 A | * | 11/1994 | Bjorklund | G02F 1/3615 359/3 |
| 5,784,507 A | * | 7/1998 | Holm-Kennedy | G01J 3/0259 250/227.23 |
| 5,978,139 A | * | 11/1999 | Hatakoshi | B82Y 10/00 359/19 |
| 6,314,220 B1 | * | 11/2001 | Mossberg | G02B 5/1819 359/558 |

(Continued)

FOREIGN PATENT DOCUMENTS

WO       2013049942 A1       4/2013

OTHER PUBLICATIONS

Preliminary Search Report filed in FR 15/50058 dated Nov. 13, 2015; 2 pages.

*Primary Examiner* — Tri T Ton
*Assistant Examiner* — Jarreas C Underwood
(74) *Attorney, Agent, or Firm* — Moreno IP Law LLC (57) ABSTRACT

An optical reflection focusing device, including a grating including an alternation of first and second regions having different refraction indexes, the grating including a plurality of sub-gratings, each including a plurality of first regions aligned along a plane parallel to the mean plane of the grating, said device including structures such that, for a collimated incident coherent light beam orthogonal to the mean plane of the grating, the rays of the beam reach with a non-zero phase shift different sub-gratings of the device.

13 Claims, 5 Drawing Sheets

(56) References Cited

U.S. PATENT DOCUMENTS

| | | | |
|---|---|---|---|
| 6,596,982 B1 * | 7/2003 | Skokan | G02B 1/11 |
| | | | 250/216 |
| 6,766,077 B2 * | 7/2004 | Packirisamy | G02B 6/124 |
| | | | 385/24 |
| 7,453,981 B2 * | 11/2008 | Baumann | A61B 6/484 |
| | | | 378/21 |
| 9,176,282 B2 * | 11/2015 | Pottier | G02B 27/4244 |
| 2003/0035215 A1 | 2/2003 | Amm et al. | |
| 2004/0240063 A1 * | 12/2004 | Delage | G02B 6/12007 |
| | | | 359/571 |
| 2007/0164221 A1 | 7/2007 | Russell | |
| 2008/0285919 A1 * | 11/2008 | Ho | G01J 3/20 |
| | | | 385/37 |
| 2013/0058370 A1 * | 3/2013 | Chang-Hasnain | B82Y 20/00 |
| | | | 372/50.11 |

* cited by examiner

OPTICAL FOCUSING DEVICE

This application claims the priority benefit of French patent application number 15/50058, filed on Jan. 6, 2015, the contents of which is hereby incorporated by reference in its entirety to the maximum extent allowable by law.

BACKGROUND

The present disclosure relates to a reflective-type optical focusing device, and more particularly aims at such a device having its focusing and reflection properties obtained by means of a resonant grating.

DISCUSSION OF THE RELATED ART

A planar reflection focusing device, comprising a non-periodic resonant grating has already been provided, particularly in article "Planar high-numerical-aperture low-loss focusing reflectors and lenses using subwavelength high contrast gratings" by Fanglu Lu et al. (7 Jun. 2010/Vol. 18, No 12/OPTICS EXPRESS 12606), herein incorporated by reference.

Figure 1:
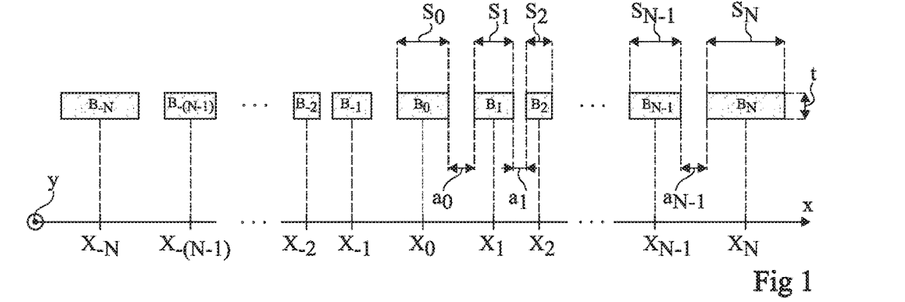
FIG. 1, previously described, is a cross-section view schematically showing an example of a reflection focusing device.
Figure 2:
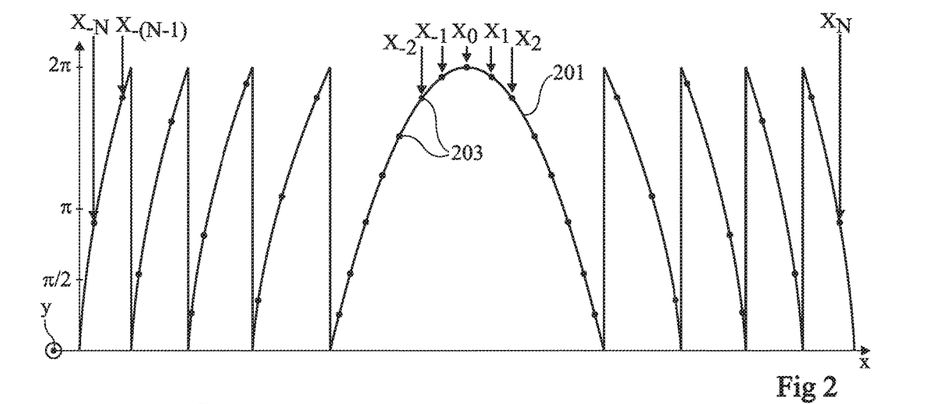
FIG. 2, previously described, is a diagram schematically showing the spatial distribution of the phase shift generated by the device of FIG. 1.

FIGS. 1 and 2 schematically illustrate the operation of such a device. More particularly, FIG. 1 is a simplified transverse cross-section view of such a device, and FIG. 2 is a diagram showing the phase shift undergone by the light reflected at different points of this device.

The device of FIG. 1 comprises a grating comprising 2N+1 parallel bars $B_{-N}$, $B_{-(N-1)}$, ..., $B_{-2}$, $B_{-1}$, $B_0$, $B_1$, $B_2$, ... $B_{N-1}$, $B_N$, N being a positive integer. Bars $B_i$ (i being an integer from −N to N) are made of a material having a relatively high refraction index, for example, AlGaAs or silicon, and are separated two by two by a region of a material of relatively refraction index, for example, air or silicon oxide. The grating of the device of FIG. 1 is non periodic, that is, different bars $B_i$ have different widths $S_i$ (according to a direction x of the mean plane of the grating transverse to bars $B_i$), and spacing $a_i$ (along direction x) between two neighboring bars $B_i$ and $B_{i+1}$ is not the same for all the grating bars. The different bars $B_i$ however all have the same thickness t, and have their upper and lower surfaces respectively aligned along a horizontal upper plane defining an upper surface of the grating, and along a horizontal lower plane defining a lower surface of the grating.

Curve 201 of FIG. 2, in full line, shows the spatial distribution, along direction x, of the phase shift that the device of FIG. 1 should ideally generate in reflection, at a specific illumination wavelength $\lambda_L$, to obtain desired focusing properties at wavelength $\lambda_L$. It should be noted that in this example, the focusing device is unidirectional (1D), that is, the incident light, after reflection on the upper or lower surface of the grating, is focused along a line parallel to the mean plane of the grating and orthogonal to direction x. In other words, the phase shift generated by the grating is constant along a direction y parallel to the mean plane of the grating and orthogonal to direction x. In the shown example, for a parallel incident coherent light beam orthogonal to the mean plane of the grating, the focusing line coincides, in vertical projection, with the central longitudinal direction of bar $B_0$.

Widths $S_i$ of bars $B_i$ and distances $a_i$ separating bars $B_i$ are selected so that, at wavelength $\lambda_L$, the grating has a relatively high reflection coefficient at any point of its surface, and generates a phase shift having a spatial distribution along direction x as close as possible to the ideal distribution shown by curve 201. Points 203 of FIG. 2 show the phase shift generated by the grating of FIG. 1 at 2N+1 points of respective coordinates $X_{-N}$, $X_{-(N-1)}$, ..., $X_{-2}$, $X_{-1}$, $X_0$, $X_1$, $X_2$, ... $X_{N-1}$, $X_N$ along direction x, respectively corresponding to the centers of the 2N+1 bars $B_i$ of the grating. Widths $S_i$ and spacings $a_i$ of the bars are selected so that points 203 are located substantially on ideal distribution curve 201. In other words, for each bar $B_i$ of the grating, a couple of values $S_i$, $a_i$ is selected to provide a specific phase shift, and the association of the 2N+1 bars $B_i$ in a non-periodic grating amounts to approximating the ideal phase-shift distribution of curve 201 with a discrete phase shift distribution shown by points 203. As explained in section 3 of Fanglu Lu et al.'s above-mentioned article, the selection of widths $S_i$ and of spacings $a_i$ enabling to obtain both a high reflectivity coefficient (to limit losses) and the desired phase shift values, may easily be achieved by using standard tools of simulation of the behavior of periodic resonant gratings. It is indeed admitted that extrapolating, to a non-periodic grating, the behavior expected for a periodic grating is a satisfactory approximation, particularly when the dimension variations between two neighboring bars of the grating are relatively low, typically in the range from 0 to 15%.

Although they have a good performance at the illumination wavelength $\lambda_L$ for which they have been designed, reflection focusing devices of the above-described type however have disadvantages.

SUMMARY

An object of an embodiment is to provide a reflection focusing device having a resonant grating, such a device overcoming all or part of the disadvantages of known devices.

Thus, an embodiment provides an optical reflection focusing device, comprising a grating comprising an alternation of first and second regions having different refraction indexes, the grating comprising a plurality of sub-gratings, each comprising a plurality of first regions aligned along a plane parallel to the mean plane of the grating, said device comprising structures such that, for a collimated incident coherent light beam orthogonal to the mean plane of the grating, the rays of the beam reach with a non-zero phase shift different sub-gratings of the device.

According to an embodiment, the structures are structures of a support element of the grating, and are such that different sub-gratings are offset by a non-zero distance along a direction orthogonal to the mean plane of the grating.

According to an embodiment, all the sub-gratings are horizontally aligned, and the grating is coated with a layer comprising, on the side of its surface opposite to the grating, structures with horizontal steps such that different sub-gratings of the device are coated with portions of different thicknesses of said layer.

According to an embodiment, the grating has a constant thickness across its entire surface.

According to an embodiment, the grating is non-periodic.

According to an embodiment, the first regions have variable widths and spacings according to at least one direction of the mean plane of the grating.

According to an embodiment, the widths and spacings of the first regions, and the heights of said structures, are selected to obtain, for a predetermined grating illumination wavelength, a reflection coefficient greater than a threshold at any point of the grating, and a predetermined spatial phase-shift distribution along said at least one direction.

According to an embodiment, the first regions are parallel bars having a square or rectangular cross-section.

According to an embodiment, the first regions are square pads.

According to an embodiment, the first regions are concentric rings.

According to an embodiment, the grating is a monomode grating, that is, it comprises a single resonance frequency.

Another embodiment provides a gas detector comprising: a light source capable of emitting a light beam in a wavelength range including a first wavelength corresponding to an absorption wavelength of the gas to be detected and a second wavelength corresponding to a reference wavelength which is not absorbed by the gas to be detected; and opposite the source, an assembly of first and second reflection focusing devices of the above-mentioned type, the first device being capable of reflecting and focusing light in a first wavelength band centered on the first wavelength, and being substantially transparent outside of this first band, and the second device being capable of reflecting and focusing light in a second wavelength band located outside of the first band and centered on the second wavelength, and being substantially transparent outside of this second band.

According to an embodiment, the detector further comprises a first photosensitive sensor arranged to only receive the light reflected by the first device, and a second photosensitive sensor arranged to only receive the light reflected by the second device.

The foregoing and other features and advantages will be discussed in detail in the following non-limiting description of specific embodiments in connection with the accompanying drawings.

DETAILED DESCRIPTION

For clarity, the same elements have been designated with the same reference numerals in the various drawings and, further, the various drawings are not to scale. Further, in the present description, unless otherwise indicated, when reference is made to terms qualifying absolute positions, such as terms "front", "rear", "top", "bottom", "left", "right", etc., or relative positions, such as terms "above", "under", "upper", "lower", etc., or to terms qualifying directions, such as terms "horizontal", "vertical", etc., such references apply to devices oriented as illustrated in the corresponding views, it being understood that, in practice, the devices may be oriented differently. Further, unless otherwise specified, expressions "approximately", "substantially", and "in the order of" mean to within 10%, preferably to within 5%.

The inventors have observed that reflection focusing devices of the type described in Fanglu Lu et al.'s above-mentioned article suffer from a lack of spectral selectivity, that is, they reflect and focus not only rays at the wavelength $\lambda_L$ for which they have been designed, but also in a relatively wide wavelength range around wavelength $\lambda_L$. This phenomenon is illustrated in FIG. 3.

Figure 3:
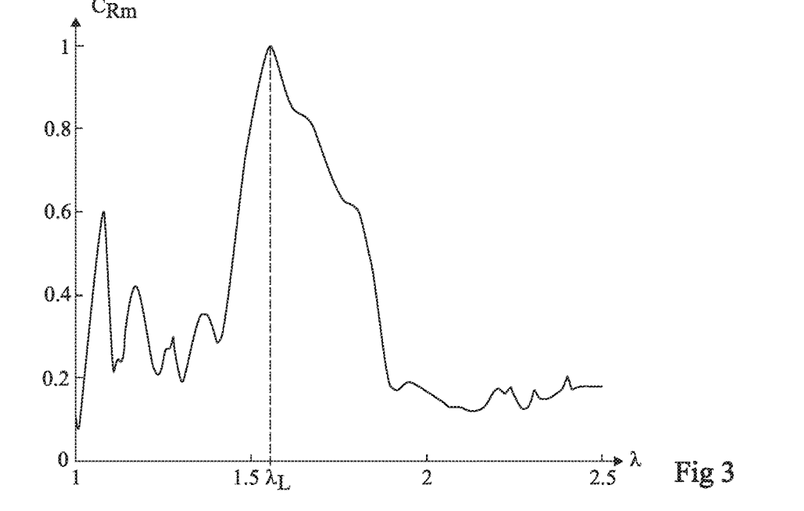
FIG. 3 is a diagram illustrating a disadvantage of the reflection focusing device described in relation with FIGS. 1 and 2.

FIG. 3 is a diagram showing the variation, according to illumination wavelength $\lambda$, of the average reflection coefficient $C_{Rm}$ of the entire grating of a device of the type described in relation with FIGS. 1 and 2 (or average of the reflection coefficients of the different grating points). As shown in FIG. 3, average reflection coefficient $C_{Rm}$ has a maximum peak at the wavelength $\lambda_L$ for which the device has been designed (1.55 µm in the shown example). However, it can be observed that the bandwidth of the device is relatively wide, that is, average reflection coefficient $C_{Rm}$ remains relatively high in a relatively wide wavelength range on either side of wavelength $\lambda_L$. Further, even far from the resonance wavelength ($\lambda < 1.4$ µm and $\lambda > 1.8$ µm), the reflection coefficient is in the order of 0.2, which means a poor rejection at the corresponding wavelengths.

Such a low spectral selectivity may raise an issue in certain applications. It would thus be desirable to have an optical reflection focusing device having a better spectral selectivity than known devices, that is, a device capable of reflecting and focusing the incident light in a predetermined narrow wavelength, this device being substantially transparent for the rest of the electromagnetic spectrum.

The inventors have identified that the non-periodic gratings used in devices of the type described in Fanglu Lu et al.'s above-mentioned article are multimode gratings, that is, they have a plurality of resonance frequencies, which at least partly explains their low spectral selectivity. The use of a grating having a limited number of resonance modes, for example, a monomode grating or a dual-mode grating, may enable to improve the spectral selectivity of the device.

However, in practice, it can be observed that if the number of resonance modes of the grating is decreased, the amplitude of the phase-shift range that the grating can be generated with a satisfactory reflectivity coefficient is accordingly decreased. More particular, with a monomode or dual-mode grating, the amplitude of the phase shift range that the grating can generate with a satisfactory reflectivity coefficient is generally smaller than $2\pi$ (that is, a full period of the incident electromagnetic wave), which limits possibilities of light focusing by the device. As an illustration, if a monomode operation is considered, it can be analytically shown, by the coupled mode theory, that whatever the resonance frequency of the grating and the quality factor of the grating, a phase variation $\Delta\phi$ ($+/-\Delta\phi/2$ around the resonance) can only be obtained at the cost of a decrease of the reflectivity coefficient by $\cos^2(\Delta\phi/2)$. Thus, if it is decided not to have the reflectivity coefficient decrease below 0.5, the amplitude of the phase-shift range capable of being obtained is $\pi/2$ (from $-\pi/4$ to $\pi/4$). Certain spatial phase-shift distributions, and accordingly certain focusing properties, then cannot be obtained. Particularly, a spatial phase-shift distribution profile of the type shown in FIG. 2, comprising phase shifts from 0 to $2\pi$, can then no longer be obtained.

According to an aspect of an embodiment, an optical reflection focusing device comprising a resonant grating comprising an alternation of regions having different refraction indexes is provided, this device comprising structures enabling to add, in certain grating portions, a constant phase shift enabling to span the $2\pi$ phase shift range necessary to perform certain optical functions.

Figure 4:
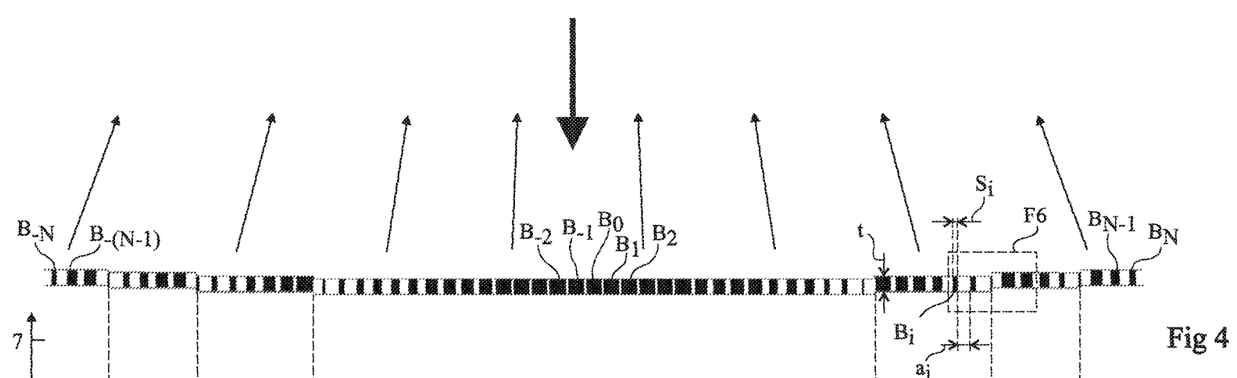
FIG. 4 is a cross-section view schematically showing an embodiment of a reflection focusing device.
Figure 6:
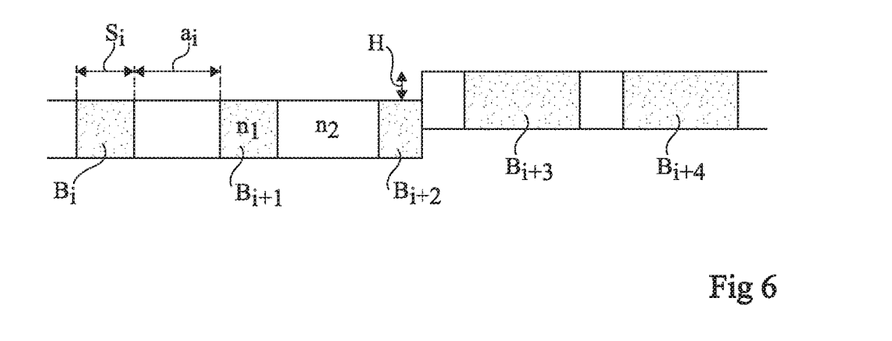
FIG. 6 is a partial simplified cross-section view showing an enlargement of a portion of the device of FIG. 4.

FIGS. 4 and 6 schematically show an embodiment of a reflection focusing device. FIG. 4 is a transverse cross-section view of the device, and FIG. 6 is an enlargement of a portion of FIG. 4, delimited by frame F6 of FIG. 4.

In this example, the focusing device is, as in the example of FIG. 1, a unidirectional (1D) focusing device.

The device of FIGS. 4 and 6 comprises a non-periodic resonant grating comprising a plurality of regions $B_i$ made of a material having a first refraction index $n_1$, for example, AlGaAs or of silicon, separated two by two by regions of a material having a second refraction index $n_2$ smaller than the first index, for example, air or silicon oxide. In this example, regions $B_i$ have the shape of parallel bars having a square or rectangular cross-section. In the shown example, the grating comprises 2N+1 parallel bars $B_{-N}$, $B_{-(N-1)}$, . . . , $B_{-2}$, $B_{-1}$, $B_0$, $B_1$, $B_2$, . . . $B_{N-1}$, $B_N$, N being a positive integer and is symmetrical with respect to the central longitudinal axis of bar $B_0$. The described embodiments are however not limited to this specific case.

Bars $B_i$ may be totally surrounded with the bar separation material. As an example, bars $B_i$ may be entirely embedded in a silicon oxide matrix comprising a substantially planar upper surface, defining an illumination surface of the device (in this case, an antireflection layer may be provided at the air/silicon oxide interface), or may be suspended to be entirely surrounded with air. The described embodiments are however not limited to these specific examples. As a variation, bars $B_i$ may be arranged on a silicon oxide support, and be laterally separated two by two and topped with air or with another material.

As in the example of FIG. 1, different bars $B_i$ of the grating have different widths $S_i$ along a direction x of the mean plane of the grating orthogonal to bars $B_i$. Further, as in the example of FIG. 1, spacing $a_i$ (along direction x) between two consecutive bars $B_i$ and $B_{i+1}$ is not the same for all the grating bars. As an example, the grating pitch, that is, the center-to-center distance between two consecutive bars $B_i$ and $B_{i+1}$ of the grating, is constant, and the filling factor of the grating for bars $B_i$ is variable along direction x. As a variation, the grating pitch is variable along direction x. Anyhow, to obtain resonant properties of the grating, the maximum pitch of the grating is smaller than wavelength $\lambda_L$ at which the grating is intended to be illuminated, for example, in the range from 0.3 to 30 µm. As an example, the maximum pitch of the grating is in the range from $\lambda_L/2$ to $\lambda_L$. Preferably, the maximum pitch of the grating is smaller than $\lambda_L/(1+\sin(\theta_i))$, where $\theta_i$ is the angle of incidence under which the grating is intended to be illuminated. It should be noted that in the present application, value $\lambda_L$ designates the wavelength of the illumination light in the incident medium, that is, in the medium crossed by the incident light before reaching the grating (which may be air, silica, or another transparent material). In the shown example, bars $B_i$ all have the same thickness or substantially the same thickness t, preferably smaller than wavelength $\lambda_L$, for example, in the range from $\lambda_L/20$ to $\lambda_L$.

The device of FIG. 4 differs from the device of FIG. 1 in that, in the example of FIG. 4, bars $B_i$ of the grating are not all horizontally aligned. More particularly, in the device of FIG. 4, the grating is divided into a plurality of sub-gratings, each comprising a plurality of consecutive bars $B_i$. The bars $B_i$ of a same sub-grating are horizontally aligned or coplanar. Coplanar here means that the bars $B_i$ of a same sub-grating have their upper surfaces arranged in a first plane parallel to the mean plane of the grating (which is a horizontal plane in the orientation of FIG. 4), and have their lower surface arranged in a same second plane parallel to the mean plane of the grating. In the device of FIG. 4, bars $B_i$ of neighboring sub-gratings are vertically offset by a non-zero distance H, preferably smaller than wavelength $\lambda_L$. In other words, the grating of the device of FIGS. 4 and 6 has a constant thickness t along direction x, but has, along direction x, a profile with horizontal steps, each step corresponding to a sub-grating of the device. As an example, the device of FIGS. 4 and 6 comprises a support element (not shown) of the grating, comprising structures such that distinct sub-gratings are vertically offset, each sub-grating being substantially horizontal.

A vertical offset H between two different sub-gratings of the device results in that, for a parallel incident coherent light beam orthogonal to the mean plane of the grating, the beam rays reach the two sub-gratings with a phase shift equal to $2\pi H/\lambda_L$. Thus, for a reflective device, the phase shift due to vertical offset H between two different sub-gratings is equal to $4\pi H/\lambda_L$. It should be noted that in practice, the incident beam is not necessarily collimated and/or perpendicular to the mean plane of the grating. As an example, the incident beam may be converging, diverging, inclined with respect to the mean plane of the grating, etc.

An advantage of the embodiment of FIG. 4 is that the combination of the phase shift due to the vertical structures of the grating, and of the phase shift due to widths $S_i$ and spacings $a_i$ of bars $B_i$ of the grating, enables to reconstruct phase-shift profiles having an amplitude greater than that which may be obtained by only varying widths $S_i$ and spacings $a_i$ of bars $B_i$. In particular, the embodiment of FIG. 4 provides a phase shift profile having an amplitude equal to $2\pi$, even when the amplitude of the phase shift range capable of being obtained by varying widths $S_i$ and spacings $a_i$ of bars $B_i$ is smaller than $2\pi$.

The number of stages of the grating of the device of FIGS. 4 and 6, as well as heights H separating neighboring sub-gratings of the device, may be freely selected according to the targeted focusing properties and to the maximum phase shift which may be obtained by the sole modification of parameters $S_i$ and $a_i$ of the grating. Preferably, each sub-grating comprises at least 5 bars $B_i$, to preserve the grating effect.

In a preferred non-limiting embodiment, height H between two neighboring sub-gratings of the device, or height of a stage, is the same for all the sub-gratings of the device. The number of stages of the device then is preferably equal to the positive integer greater than or equal to $2\pi/\Delta\phi$, where $\Delta\phi$ is the maximum phase shift which may be obtained by the only modifying parameters $S_i$ and $a_i$ of the grating. It can generally be observed that to keep a satisfactory reflectivity level, for example, greater than 0.5, $\Delta\phi$ is approximately equal to $nb_{modes}*\pi/2$, where $nb_{modes}$ designates the number of resonance modes of the grating. In the shown example, the device comprises 4 stages separated two by two by a same height $H=\lambda_L/8$, where $\lambda_L$ is the wavelength at which the grating is intended to be illuminated, which translates as a reflection phase shift (return travel) of approximately π/2 between two successive stages.

Although an embodiment where each step of the grating is formed at the interface between a bar $B_i$ and the material laterally separating bars $B_i$ has been shown in FIGS. 4 and 6, the described embodiments are not limited to this specific case. As a variation, the grating steps may be formed at an intermediate distance (along direction x) between two neighboring bars $B_i$, for example, at mid-distance between two neighboring bars $B_i$, or in a bar $B_i$ (which then extends over two stages).

Figure 5:
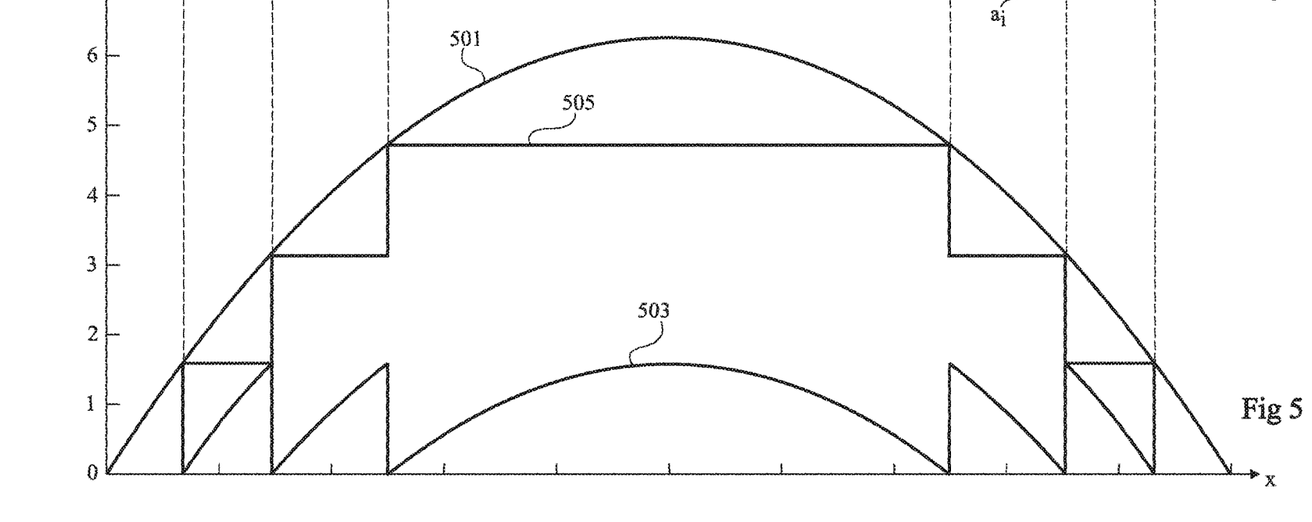
FIG. 5 is a diagram schematically showing the spatial distribution generated by the device of FIG. 4.

FIG. 5 is a diagram schematically showing the spatial distribution of the phase shift generated by the device of FIGS. 4 and 6. More particularly, curve 501 of FIG. 5 shows the spatial distribution, along direction x, of the phase shift that the device of FIGS. 4 and 6 should generate in reflection at wavelength $\lambda_L$ at which the grating is intended to be illuminated, to obtain desired focusing properties at this wavelength. In this example, the amplitude of the range of phase shifts to be obtained is 2π, and the amplitude of the phase shifts which may be obtained by varying parameters $S_i$ and $a_i$ of the grating is π/2. The stepped structure of the grating is provided so as to add, in each sub-grating, a constant phase shift selected from among four phase shift levels, respectively, 0, π/2, π, and 3π/2, to the phase shift of the grating. The spatial distribution of the phase shifts to be generated may be divided into two contributions, the first one, illustrated by curve 503 of FIG. 5, originating from the variations of parameters $S_i$ and $a_i$ of the grating along direction x, and the second one, illustrated by curve 505 of FIG. 5, originating from the stepped structure of the grating. Combining these two effects provides the desired phase shift profile, illustrated by curve 501. Widths $S_i$ and spacings $a_i$ of bars $B_i$ are selected similarly to what has been described in relation with FIG. 2, so that, at wavelength $\lambda_L$, and in the absence of the vertical stepped structures, the grating has a relatively high reflection coefficient at any point of its surface, and generates a phase shift having its spatial distribution approximating the ideal distribution represented by curve 503.

Figure 7:
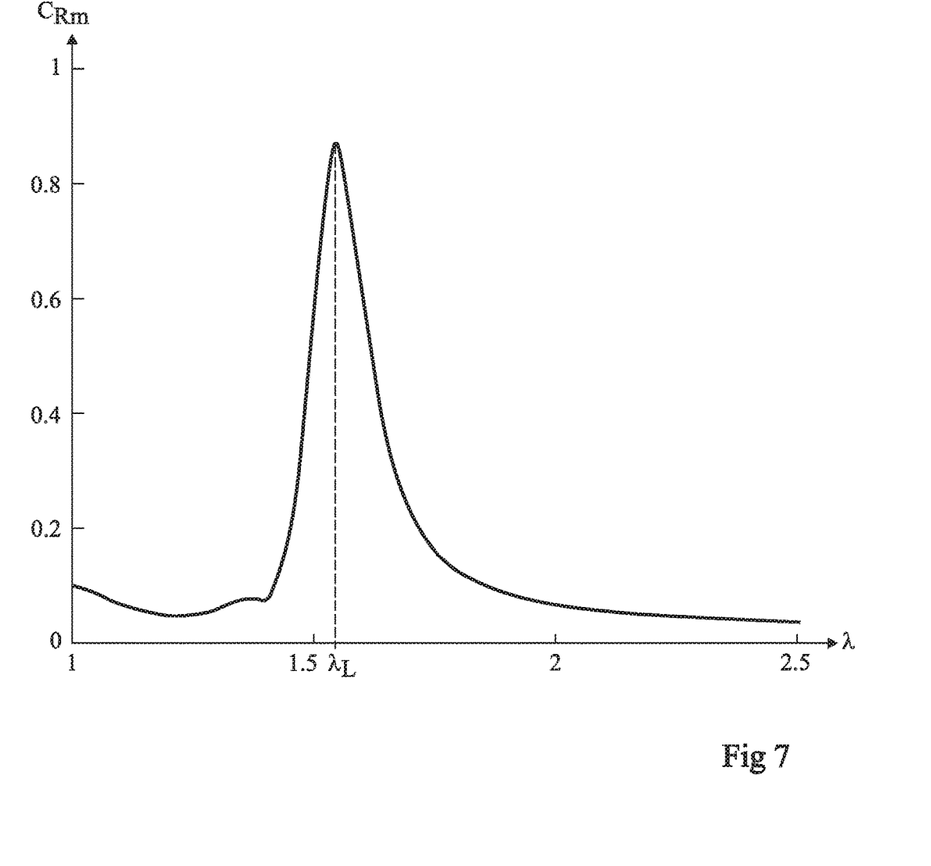
FIG. 7 is a diagram schematically illustrating the wavelength behavior of the device of FIG. 4.

Advantageously, the grating of the device of FIGS. 4 and 6 has a limited number of resonance modes, for example, a single mode or two resonance modes, which enables to obtain a reflection focusing device having a larger spectral selectivity than with known devices, as illustrated in FIG. 7, which will be described in further detail hereafter.

The forming of a grating comprising a limited number of resonance modes, for example, a monomode grating, is within the abilities of those skilled in the art and will not be described in detail. As an example, a mapping representative of the variation, according to width $S_i$ and to spacing $a_i$ of the bars, of the reflection coefficient and of the phase shift generated by a grating of the considered type, may first be performed. An example of such a mapping is particularly shown in FIG. 2 in Fanglu Lu et al.'s above-mentioned article. Based on this mapping, a path of points of coordinates ($S_i$, $a_i$) may be selected to obtain the desired reflectivity and phase-shift distribution. To form a monomode grating, the selected path preferably follows a continuous reflectivity profile, that is, in particular, unlike what has been shown in FIG. 2 of the above-mentioned article, it remains in the vicinity of a same continuous curve of strong reflectivity, intersecting this curve to obtain the desired phase shifts by minimizing reflectivity variations.

As a non-limiting example, to favor the obtaining a grating having a high spectral selectivity, the grating may have the following characteristics: a pitch greater than $0.8*\lambda_L$, which amounts to being just under the diffraction limit; and/or a factor of filling of the grating with bars $B_i$ smaller than 0.2 or greater than 0.8, that is, a relatively fine grating to avoid mode degeneracies (likely to occur for filling factors close to 0.5); and/or a thickness t of bars $B_i$ smaller than $\lambda_L/2$, to limit to one the number of vertically-supported modes. The described embodiments are however not limited to these specific examples of dimensional parameters of the grating.

FIG. 7 is a diagram showing the variation, according to illumination wavelength λ, of the average reflection coefficient $C_{Rm}$ of the entire grating of a device of the type described in relation with FIGS. 4 and 6 (or average of the reflection coefficients of the different grating points). More particularly, the case of a device designed for an illumination wavelength $\lambda_L=1.55$ μm, having a 1-mm width and a 2.5-cm focal distance, and where the grating is monomode, is here considered. As shown in FIG. 7, average reflection coefficient $C_{Rm}$ exhibits a maximum peak at wavelength $\lambda_L$. It can further be observed in FIG. 7 that, as compared with the example of FIG. 3, the device has a high spectral selectivity, that is, the device reflects and focuses only the light located in a narrow wavelength range centered on wavelength $\lambda_L$, for example, a wavelength range smaller than 250 nm including wavelength $\lambda_L$, and is transparent or almost transparent (reflection coefficient smaller than 0.2) outside of this range. Such a device thus forms a particularly compact spectral sorter capable of having applications in many fields (imaging, sensors, beam shaping, etc.). A non-limiting example of application of such a device to a gas sensor will be described hereafter in relation with FIG. 11.

The described embodiments are however not limited to the case where the grating used comprises a limited number of resonance modes. More generally, an advantage of the embodiment of FIGS. 4 and 6 is that it provides, as compared with known devices of the type described in Fanglu Lu et al.'s article, an additional phase-shift adjustment parameter, to achieve the desired phase shift distribution. As an example, even when a strong spectral selectivity is not required and the grating has a relatively large number of resonance modes, for example, greater than or equal to four, which would enable to cover a 2π phase shift range with a good reflectivity coefficient, the grating may be stepped, for example, to relax the constraints relative to the selection of the pairs of values $S_i$, $a_i$, for example, to facilitate the grating manufacturing or to control the average index of the grating.

Figure 8:
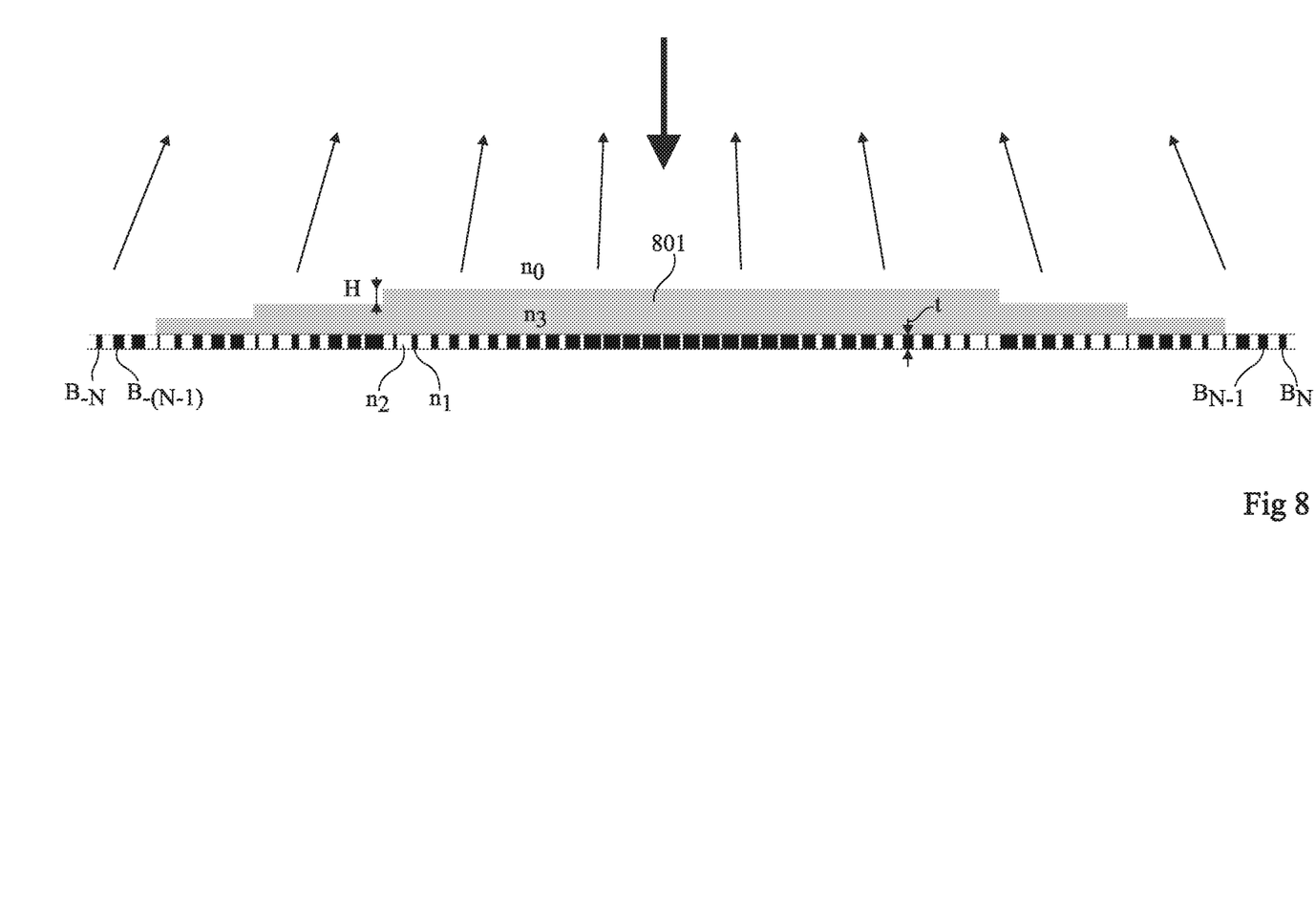
FIG. 8 is a cross-section view schematically showing an alternative embodiment of the reflection focusing device of FIG. 4.

FIG. 8 is a transverse cross-section view schematically showing an alternative embodiment of the device of FIGS. 4 and 6. The device of FIG. 8 has common points with the device of FIGS. 4 and 6. In the following, only the differences between the device of FIG. 8 and the device of FIGS. 4 and 6 will be underlined.

The device of FIG. 8 differs from the device of FIGS. 4 and 6 in that, in the device of FIG. 8, the grating formed by bars $B_i$ is not itself structured. In other words, in the example of FIG. 8, all the bars $B_i$ of the grating are horizontally aligned or coplanar.

In the device of FIG. 8, the grating is coated, on its upper surface side, with a layer 801 of a material having refraction index $n_3$, different from index $n_0$ of the incident medium where the light propagates before reaching the upper surface of the device. As a non-limiting example, index $n_3$ may be identical to index $n_2$ of the material laterally separating bars $B_i$. Preferably, an antireflection layer, not shown, coats the upper surface of layer 801, at the interface between the mediums of indexes $n_0$ and $n_3$.

Layer 801 comprises, on its upper surface side, structures defining, along direction x, horizontal steps. Thus, different portions of the grating, corresponding to the sub-gratings of the example of FIGS. 4 to 6, are topped with different thicknesses of layer 801.

Thickness difference H between two steps of different thicknesses of layer 801 results in introducing a constant phase shift between the two corresponding underlying sub-gratings.

Thus, similarly to what has been described in relation with FIGS. 4 to 6, the combination of the phase shift due to the vertical structuring of the device (i.e. the structures of layer 801 in this example) and of the phase shift due to parameters $S_i$ and $a_i$ of the grating enables to reconstruct phase shift profiles having an amplitude greater than that which may be obtained by only varying parameters $S_i$ and $a_i$.

It should be noted that in the examples described in relation with FIGS. 4 to 8, the grating of the device is formed by parallel bars $B_i$ of refraction index $n_1$, laterally separated by a material of index $n_2$. For the device to properly operate, the incident light should preferably be polarized along a rectilinear direction parallel to bars $B_i$. As a variation, each bar $B_i$ may be divided into rectangular pads regularly spaced apart along direction y of the device, so that the device is compatible with light polarized orthogonally to bars $B_i$.

Further, although only embodiments of unidirectional (1D) focusing devices have been detailed hereabove, the described embodiments may be adapted to bidirectional focusing devices, that is, devices capable of focusing the light reflected at a point.

Figure 9:
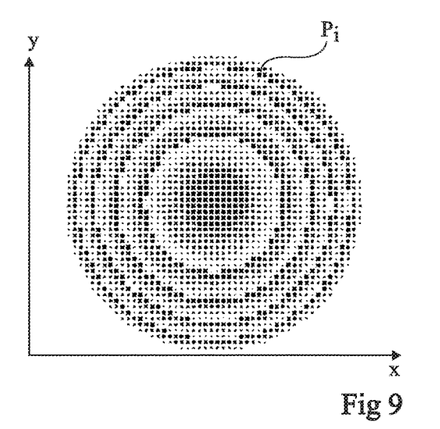
FIG. 9 is a top view schematically showing an alternative bidimensional embodiment of a reflection focusing device.
Figure 10:
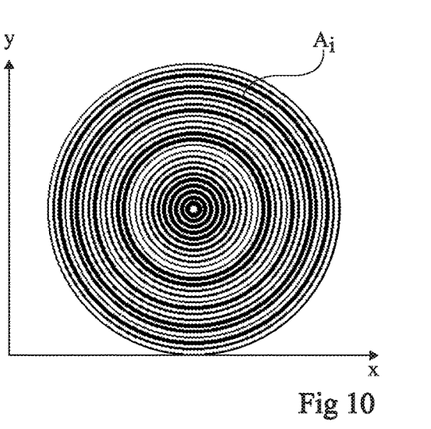
FIG. 10 is a top view schematically showing another alternative bidimensional embodiment of a reflection focusing device.

FIGS. 9 and 10 are top views schematically showing two alternative bidimensional embodiments of a reflection focusing device of the type described in relation with FIGS. 4 to 8.

In the example of FIG. 9, the grating is formed of square pads $P_i$ of refraction index n1, separated two by two by a material of index n2, the widths and the spacings of the pads varying along orthogonal directions x and y of the mean plane of the device. As in the examples of FIGS. 4 to 8, the device may be divided into sub-gratings, each comprising a plurality of neighboring pads $P_i$, and may comprise structures (not shown in FIG. 9) such that, for a collimated incident coherent light beam orthogonal to the mean plane of the grating, the beam rays reach with a non-zero phase shift different sub-gratings of the device. The device of FIG. 9 is capable of operating with rectilinearly-polarized light, whatever the polarization direction.

In the example of FIG. 10, the grating is formed of concentric rings $A_i$ of refraction index n1, separated two by two by a material of index n2, the widths and spacings of the rings varying along a radial direction. As in the examples of FIGS. 4 to 8, the device may be divided into sub-gratings each comprising a plurality of rings $A_i$, and may comprise structures (not shown in FIG. 10) such that, for a parallel incident coherent light beam orthogonal to the mean plane of the grating, the beam rays reach with a non-zero phase shift different sub-gratings of the device. The device of FIG. 10 is capable of operating with light having a radial or azimuthal polarization.

Figure 11:
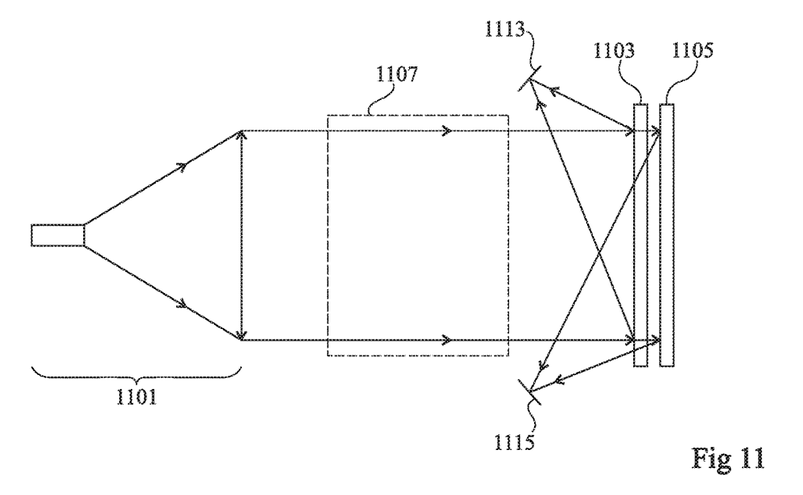
FIG. 11 is a cross-section view schematically showing an embodiment of a gas detector using a reflection focusing device of the type described in relation with FIGS. 4 to 10.

FIG. 11 schematically shows an example of application of a chromatic reflection focusing device of the type described in relation with FIGS. 4 to 10 to an optical gas detector. An optical detector which detects the presence and possibly measures the content of a gas, for example, $CO_2$ or CO, in an atmosphere, by measuring the absorption of a light beam at a wavelength corresponding to an absorption line of the considered gas, is here more specifically considered.

The detector of FIG. 11 comprises a light source 1101, for example, an infrared source, capable of emitting a collimated light beam in a relatively wide wavelength range including wavelength $\lambda_m$ of an absorption line characteristic of the gas to be detected.

The detector of FIG. 11 further comprises first and second chromatic reflection focusing devices 1103 and 1105, of the type described in relation with FIGS. 4 to 10. In this example, devices 1103 and 1105 are arranged opposite each other, in parallel planes substantially orthogonal to the beam emitted by source 1101. In the shown example, device 1103 is upstream of device 1105, that is, after having crossed a portion 1107 of the atmosphere capable of containing the gas to be detected, the beam emitted by source 1101 first reaches device 1103, after which the portion of the beam transmitted by device 1103 reaches device 1105.

Device 1103 is capable of reflecting and focusing the light in a narrow wavelength band centered on measurement wavelength $\lambda_m$, and is substantially transparent outside of this band. Device 1105 is capable of reflecting and focusing the light in a narrow wavelength band centered on a reference wavelength $\lambda_r$, outside of the band where device 1103 is reflective and which does not correspond to an absorption wavelength of the gas to be detected, and is substantially transparent outside of this reference band.

To avoid superposing the images reflected by devices 1103 and 1105, devices 1103 and 1105 are capable of focusing the reflected light along different axes, different from the axis of the incident beam originating from source 1101.

The detector of FIG. 11 further comprises a first photosensitive sensor 1113 arranged to only receive the light reflected by device 1103, and a second photosensitive sensor 1115 arranged to only receive the light reflected by device 1105.

In other words, device 1103 behaves as a focusing mirror having its focus centered on sensor 1113, and which would have its axis parallel to the incident collimated beam, and device 1105 behaves as a focusing mirror having its focus centered on sensor 1115, and having an axis parallel to the incident collimated beam.

By comparing the intensities of the light signals received by sensors 1113 and 1115, it is possible to detect the presence of, and possibly to measure the content of the gas to be detected.

An advantage of such a gas detector is that it enables to do away with the filters conventionally arranged in front of the photosensitive sensors of known gas detectors, which particularly enables to improve the light output as compared with known sensors.

It should be noted that in the example of FIG. 11, the light transmitted by device 1103 may undergo a phase shift due to the grating and to the structuring of device 1103. On design of device 1105, this phase shift should be taken into account to define the spatial phase shift distribution which should be generated by device 1105.

Preferably, the distance between devices 1103 and 1105 is relatively short, for example, shorter than twice the average illumination wavelength, so that the propagation of the beam transmitted by device 1103 can be considered to be substantially orthogonal to device 1105.

Various alternative embodiments of the gas detector of FIG. 11 may be provided. In particular, the positions of devices 1103 and 1105 may be exchanged.

Specific embodiments have been described. Various alterations, modifications, and improvements will readily occur to those skilled in the art. In particular, the described embodiments are not limited to the specific example of application to a gas detector of the reflection focusing devices of the type described in relation with FIGS. 4 to 10.

As an example, such devices may be used in the field of multiple junction photovoltaic cells. Conventionally, such cells comprise a plurality of stacked PN junctions made of different semiconductor materials, sensitive to different illumination wavelengths. The use of a spectral sorter based on chromatic reflection focusing devices of the type described in relation with FIGS. 4 to 10 may advantageously enable, instead of stacking the different junctions, to juxtapose the junctions next to one another, thus facilitating the cell manufacturing. Such a reflective spectral sorter may in particular be used to distribute the different wavelengths of solar radiation towards the most appropriate junctions.

Such alterations, modifications, and improvements are intended to be part of this disclosure, and are intended to be within the spirit and the scope of the present invention. Accordingly, the foregoing description is by way of example only and is not intended to be limiting. The present invention is limited only as defined in the following claims and the equivalents thereto.

What is claimed is:

1. An optical reflection focusing device, comprising a grating comprising an alternation of first ($B_i$; $P_i$; $A_i$) and second regions having different refraction indexes (n1, n2), the grating comprising a plurality of sub-gratings each comprising a plurality of first ($B_i$; $P_i$; $A_i$) and second coplanar regions aligned along a plane parallel to the mean plane of the grating, said device comprising structures such that, for a collimated incident coherent light beam orthogonal to the mean plane of the grating, the rays of the beam reach with a non-zero phase shift different sub-gratings of the device;
   wherein the structures are structures of a support element of the grating, and are such that different sub-gratings are offset by a non-zero distance along a direction a direction orthogonal to the mean plane of the grating.

2. An optical reflection focusing device, comprising a grating comprising an alternation of first and second regions having different refraction indexes, the grating comprising a plurality of sub-gratings each comprising a plurality of first and second coplanar regions aligned along a plane parallel to the mean plane of the grating, said device comprising structures such that, for a collimated incident coherent light beam orthogonal to the mean plane of the grating, the rays of the beam reach with a non-zero phase shift different sub-gratings of the device;
   wherein all the sub-gratings are horizontally aligned, and wherein the grating is coated with a layer (801) comprising, on the side of its surface opposite to the grating, structures with horizontal steps such that different sub-gratings of the device are coated with portions of different thicknesses of said layer.

3. The device of claim 1, wherein the grating has a constant thickness (t) across its entire surface.

4. The device of claim 1, wherein the grating is non-periodic.

5. The device of claim 1, wherein the first regions ($B_i$; $P_i$; $A_i$) have variable widths ($S_i$) and spacings ($a_i$) along at least one direction (x; y) of the mean plane of the grating.

6. The device of claim 5, wherein the widths ($S_i$) and the spacings ($a_i$) of the first regions ($B_i$; $P_i$; $A_i$) and the heights (H) of said structures are selected to obtain, for a predetermined grating illumination wavelength $\lambda_L$, a reflection coefficient greater than 0.5 at any point of the grating, and a predetermined spatial phase-shift distribution along said at least one direction (x; y).

7. The device of claim 6, wherein the maximum pitch of the grating is smaller than said illumination wavelength $\lambda_L$ of the grating.

8. The device of claim 6, wherein the maximal pitch of the grating is smaller than $\lambda_L/(1+\sin(\theta_i))$, where $\theta_i$ is the angle of incidence under which the grating is intended to be illuminated.

9. The device of claim 6, wherein the widths ($S_i$) and spacings ($a_i$) of the first regions ($B_i$, $P_i$, $A_i$), and the heights (H) of said structures are selected to obtain, outside of a wavelength band having a width smaller than 250 nm including said illumination wavelength $\lambda_L$ of the grating, a reflection coefficient smaller than 0.2 at any point of the grating.

10. The device of claim 1, wherein said first regions ($A_i$; $P_i$; $B_i$) are:
   parallel bars having a square or rectangular cross-section; or
   square pads; or
   concentric rings.

11. The device of claim 1, wherein said grating is a monomode grating, that is, it comprises a single resonance frequency.

12. A gas detector comprising:
   a light source (1101) emitting a light beam in a wavelength range including a first wavelength ($\lambda_m$) corresponding to an absorption wavelength of the gas to be detected and a second wavelength ($\lambda_r$) corresponding to a reference wavelength which is not absorbed by the gas to be detected; and
   opposite the source, an assembly of first (1103) and second (1105) reflection focusing devices as claimed in claim 1, the first device (1103) reflecting and focusing light in a first wavelength band centered on said first wavelength ($\lambda_m$), and being substantially transparent outside of this first band, and the second device (1105) reflecting and focusing light in a second wavelength band located outside of the first band and centered on said second wavelength ($\lambda_r$), and being substantially transparent outside of this second band.

13. The gas detector of claim 12, further comprising a first photosensitive sensor (1113) arranged to only receive the light reflected by the first device (1103), and a second photosensitive sensor (1115) arranged to only receive the light reflected by the second device (1105).

* * * * *